(12) United States Patent
Bradley et al.

(10) Patent No.: US 11,376,435 B2
(45) Date of Patent: Jul. 5, 2022

(54) SYSTEM AND METHOD FOR SHAPED PHASED CURRENT DELIVERY

(71) Applicant: Boston Scientific Neuromodulation Corporation, Valencia, CA (US)

(72) Inventors: Kerry Bradley, Glendale, CA (US); Rafael Carbunaru, Valley Village, CA (US); Dongchul Lee, Agua Dulce, CA (US); Michael A. Moffitt, Solon, OH (US); Christopher Ewan Gillespie, Stevenson Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 356 days.

(21) Appl. No.: 16/437,478

(22) Filed: Jun. 11, 2019

(65) Prior Publication Data

US 2019/0290906 A1    Sep. 26, 2019

Related U.S. Application Data

(63) Continuation-in-part of application No. 15/420,745, filed on Jan. 31, 2017, now Pat. No. 10,589,099, and
(Continued)

(51) Int. Cl.
*A61N 1/36* (2006.01)
*A61N 1/372* (2006.01)

(52) U.S. Cl.
CPC ..... *A61N 1/36071* (2013.01); *A61N 1/36171* (2013.01); *A61N 1/36189* (2013.01);
(Continued)

(58) Field of Classification Search
None
See application file for complete search history.

(56) References Cited

U.S. PATENT DOCUMENTS

| 4,338,945 A | 7/1982 | Kosugi et al. |
| 4,612,934 A | 9/1986 | Borkan |

(Continued)

FOREIGN PATENT DOCUMENTS

| EP | 0781153 B1 | 2/2003 |
| EP | 2190527 B1 | 7/2013 |

(Continued)

OTHER PUBLICATIONS

US 9,561,368 B1, 02/2017, Lee et al. (withdrawn)
(Continued)

*Primary Examiner* — Michael W Kahelin
(74) *Attorney, Agent, or Firm* — Schwegman Lundberg & Woessner, P.A.

(57) ABSTRACT

A method of treating an ailment suffered by a patient using one or more electrodes adjacent spinal column tissue of the patient, comprises delivering electrical modulation energy from the one or more electrodes to the spinal column tissue in accordance with a continuous bi-phasic waveform having a positive phase and a negative phase, thereby modulating the spinal column tissue to treat the ailment. An implantable electrical modulation system, comprises one or more electrical terminals configured for being coupled to one or more modulation leads, output modulation circuitry capable of outputting electrical modulation energy to the electrical terminal(s) in accordance with a continuous bi-phasic waveform, and control circuitry configured for modifying a shape of the continuous bi-phasic waveform, thereby changing the characteristics of the electrical modulation energy outputted to the electrode(s).

20 Claims, 8 Drawing Sheets

Related U.S. Application Data a continuation-in-part of application No. 15/269,591, filed on Sep. 19, 2016, now abandoned, said application No. 15/420,745 is a continuation of application No. 14/997,692, filed on Jan. 18, 2016, now Pat. No. 9,849,285, said application No. 15/269,591 is a continuation of application No. 13/893,094, filed on May 13, 2013, now abandoned, said application No. 14/997,692 is a continuation of application No. 13/231,493, filed on Sep. 13, 2011, now Pat. No. 9,238,138, which is a continuation of application No. 12/175,758, filed on Jul. 18, 2008, now Pat. No. 8,036,754.

(60) Provisional application No. 61/646,773, filed on May 14, 2012, provisional application No. 60/951,177, filed on Jul. 20, 2007.

(52) U.S. Cl.
CPC ..... *A61N 1/36192* (2013.01); *A61N 1/37223* (2013.01); *A61N 1/37241* (2013.01); *A61N 1/37247* (2013.01)

(56) References Cited

U.S. PATENT DOCUMENTS

| | | | |
|---|---|---|---|
| 4,821,724 A | 4/1989 | Whigham et al. | |
| 5,184,616 A | 2/1993 | Weiss | |
| 5,222,494 A | 6/1993 | Baker, Jr. | |
| 5,300,096 A | 4/1994 | Hall et al. | |
| 5,725,560 A * | 3/1998 | Brink | A61N 1/3906 607/5 |
| 5,782,874 A | 7/1998 | Loos | |
| 6,052,624 A | 4/2000 | Mann | |
| 6,246,912 B1 | 6/2001 | Sluijter et al. | |
| 6,393,325 B1 | 5/2002 | Mann et al. | |
| 781,153 A1 | 2/2003 | Hrdlicka et al. | |
| 6,516,227 B1 | 2/2003 | Meadows et al. | |
| 6,560,490 B2 | 5/2003 | Grill et al. | |
| 6,671,556 B2 | 12/2003 | Osorio et al. | |
| 6,711,442 B1 | 3/2004 | Swerdlow et al. | |
| 6,731,981 B1 | 5/2004 | Hemmingsson et al. | |
| 6,845,271 B2 | 1/2005 | Fang et al. | |
| 6,850,802 B2 | 2/2005 | Holsheimer | |
| 6,895,280 B2 | 5/2005 | Meadows et al. | |
| 6,909,917 B2 | 6/2005 | Woods et al. | |
| 6,934,580 B1 | 8/2005 | Osorio et al. | |
| 6,993,384 B2 | 1/2006 | Bradley et al. | |
| 7,076,307 B2 | 7/2006 | Boveja et al. | |
| 7,149,579 B1 | 12/2006 | Koh et al. | |
| 7,317,948 B1 | 1/2008 | King et al. | |
| 7,389,145 B2 * | 6/2008 | Kilgore | A61N 1/32 607/46 |
| 7,539,538 B2 | 5/2009 | Parramon et al. | |
| 7,593,775 B2 | 9/2009 | Campos et al. | |
| 8,010,198 B2 | 8/2011 | Libbus et al. | |
| 8,036,754 B2 | 10/2011 | Lee et al. | |
| 8,175,705 B2 | 5/2012 | Libbus | |
| 8,249,711 B2 | 8/2012 | Libbus et al. | |
| 8,401,653 B2 | 3/2013 | Libbus et al. | |
| 8,644,947 B2 | 2/2014 | Zhu et al. | |
| 8,694,104 B2 | 4/2014 | Libbus et al. | |
| 8,706,250 B2 | 4/2014 | Zhu et al. | |
| 8,788,048 B2 | 7/2014 | Bennett et al. | |
| 8,788,054 B2 | 7/2014 | Kothandaraman et al. | |
| 8,909,350 B2 | 12/2014 | Lee | |
| 9,138,582 B2 | 9/2015 | Doan | |
| 9,174,053 B2 | 11/2015 | Zhu | |
| 9,238,138 B2 | 1/2016 | Lee et al. | |
| 9,827,422 B2 | 11/2017 | Zhu | |
| 9,849,285 B2 | 12/2017 | Lee et al. | |
| 9,950,170 B2 | 4/2018 | Libbus et al. | |
| 10,589,099 B2 | 3/2020 | Lee et al. | |
| 2002/0019650 A1 | 2/2002 | Craggs et al. | |
| 2002/0052632 A1 | 5/2002 | Ben-Haim et al. | |
| 2002/0055779 A1 | 5/2002 | Andrews | |
| 2002/0123771 A1 | 9/2002 | Ideker et al. | |
| 2002/0143365 A1 | 10/2002 | Herbst | |
| 2003/0100931 A1 * | 5/2003 | Mullett | A61N 1/36071 607/46 |
| 2003/0139781 A1 | 7/2003 | Bradley et al. | |
| 2004/0186521 A1 | 9/2004 | Rubin et al. | |
| 2004/0210271 A1 | 10/2004 | Campen et al. | |
| 2004/0267333 A1 | 12/2004 | Kronberg | |
| 2005/0267546 A1 | 12/2005 | Parramon et al. | |
| 2006/0069415 A1 | 3/2006 | Cameron et al. | |
| 2006/0149337 A1 | 7/2006 | John | |
| 2006/0173493 A1 | 8/2006 | Armstrong et al. | |
| 2006/0173494 A1 | 8/2006 | Randolph et al. | |
| 2006/0265027 A1 | 11/2006 | Vaingast et al. | |
| 2007/0027486 A1 | 2/2007 | Armstrong | |
| 2007/0027508 A1 | 2/2007 | Cowan | |
| 2007/0038250 A1 | 2/2007 | He et al. | |
| 2007/0043401 A1 | 2/2007 | John | |
| 2007/0066971 A1 | 3/2007 | Podhajsky | |
| 2007/0097593 A1 | 5/2007 | Armstrong | |
| 2007/0129720 A1 | 6/2007 | Demarais et al. | |
| 2007/0142874 A1 | 6/2007 | John | |
| 2007/0167985 A1 | 7/2007 | Kirby | |
| 2007/0213783 A1 | 9/2007 | Pless | |
| 2007/0225765 A1 | 9/2007 | King | |
| 2007/0299482 A1 | 12/2007 | Littlewood et al. | |
| 2008/0051839 A1 * | 2/2008 | Libbus | A61N 1/36132 607/2 |
| 2008/0065167 A1 | 3/2008 | Boggs, II et al. | |
| 2008/0071321 A1 | 3/2008 | Boggs, II et al. | |
| 2008/0243204 A1 | 10/2008 | Uthman et al. | |
| 2009/0024189 A1 * | 1/2009 | Lee | A61N 1/37247 607/66 |
| 2010/0204741 A1 * | 8/2010 | Tweden | A61N 1/3787 607/3 |
| 2010/0274314 A1 | 10/2010 | Alataris et al. | |
| 2011/0009923 A1 | 1/2011 | Lee | |
| 2012/0004707 A1 | 1/2012 | Lee et al. | |
| 2012/0215279 A1 | 8/2012 | Libbus | |
| 2013/0131760 A1 | 5/2013 | Rao et al. | |
| 2013/0304152 A1 | 11/2013 | Bradley et al. | |
| 2014/0088674 A1 | 3/2014 | Bradley | |
| 2014/0002221 A1 | 8/2014 | Libbus et al. | |
| 2014/0243925 A1 | 8/2014 | Kothandaraman | |
| 2014/0257428 A1 | 9/2014 | Zhu | |
| 2014/0364920 A1 | 12/2014 | Doan et al. | |
| 2014/0364921 A1 | 12/2014 | Legay et al. | |
| 2016/0001087 A1 | 1/2016 | Moffitt | |
| 2016/0106985 A1 | 4/2016 | Zhu | |
| 2016/0129247 A1 | 5/2016 | Lee et al. | |
| 2017/0000101 A1 | 1/2017 | Bradley et al. | |
| 2017/0136243 A1 | 5/2017 | Lee | |
| 2019/0381319 A1 | 12/2019 | Lee et al. | |

FOREIGN PATENT DOCUMENTS

| | | |
|---|---|---|
| EP | 2586491 B1 | 8/2016 |
| JP | 2005279001 A | 10/2005 |
| JP | 2013163112 A | 8/2013 |
| WO | WO-8707511 A2 | 12/1987 |
| WO | WO-9609852 A1 | 4/1996 |
| WO | WO-9715351 A1 | 5/1997 |
| WO | WO-2007048087 A2 | 4/2007 |
| WO | WO-2007048087 A3 | 4/2007 |
| WO | WO-2008017055 A2 | 2/2008 |
| WO | WO-2008017055 A3 | 2/2008 |
| WO | WO-2009015005 | 1/2009 |

OTHER PUBLICATIONS

U.S. Appl. No. 15/420,745, filed Jan. 31, 2017, Neural Stimulation System to Deliver Different Pulse Types.
U.S. Appl. No. 13/893,094, filed May 13, 2013, System and Method for Shaped Phased Current Delivery.

(56) References Cited

OTHER PUBLICATIONS

U.S. Appl. No. 15/269,591, filed Sep. 19, 2016, System and Method for Shaped Phased Current Delivery.

"U.S. Appl. No. 12/175,758, Non Final Office Action dated Mar. 3, 2011", 11 pgs.

"U.S. Appl. No. 12/175,758, Notice of Allowance dated Jun. 10, 2011", 7 pgs.

"U.S. Appl. No. 12/175,758, filed Apr. 12, 2011 to Non Final Office Action dated Mar. 3, 2011", 8 pgs.

"U.S. Appl. No. 13/231,493, Final Office Action dated Sep. 11, 2014", 9 pgs.

"U.S. Appl. No. 13/231,493, Non Final Office Action dated Mar. 12, 2015", 9 pgs.

"U.S. Appl. No. 13/231,493, Non Final Office Action dated Apr. 17, 2014", 9 pgs.

"U.S. Appl. No. 13/231,493, Notice of Allowance dated Sep. 9, 2015", 5 pgs.

"U.S. Appl. No. 13/231,493, Preliminary Amendment filed Sep. 13, 2011", 8 pgs.

"U.S. Appl. No. 13/231,493, filed Jun. 6, 2014 to Non Final Office Action dated Apr. 17, 2014", 11 pgs.

"U.S. Appl. No. 13/231,493, filed Jun. 23, 2015 to Non Final Office Action dated Mar. 12, 2015", 11 pgs.

"U.S. Appl. No. 13/893,094, Advisory Action dated Sep. 15, 2016", 6 pgs.

"U.S. Appl. No. 13/893,094, Advisory Action dated Dec. 30, 2015", 4 pgs.

"U.S. Appl. No. 13/893,094, Final Office Action dated Jun. 17, 2016", 10 pgs.

"U.S. Appl. No. 13/893,094, Final Office Action dated Oct. 20, 2015", 10 pgs.

"U.S. Appl. No. 13/893,094, Non Final Office Action dated Jan. 22, 2016", 11 pgs.

"U.S. Appl. No. 13/893,094, Non Final Office Action dated May 27, 2015", 9 pgs.

"U.S. Appl. No. 13/893,094, filed Apr. 21, 2016 to Non Final Office Action dated Jan. 22, 2016", 10 pgs.

"U.S. Appl. No. 13/893,094, Response filed May 11, 2015 to Restriction Requirement dated Mar. 10, 2015", 7 pgs.

"U.S. Appl. No. 13/893,094, Response filed Aug. 26, 2015 to Non Final Office Action dated May 27, 2015", 9 pgs.

"U.S. Appl. No. 13/893,094, filed Aug. 26, 2016 to Final Office Action dated Jun. 17, 2016", 8 pgs.

"U.S. Appl. No. 13/893,094, filed Dec. 16, 2015 to Final Office Action dated Oct. 20, 2015", 9 pgs.

"U.S. Appl. No. 13/893,094, Restriction Requirement dated Mar. 10, 2015", 7 pgs.

"U.S. Appl. No. 14/997,692, Corrected Notice of Allowance dated Nov. 20, 2017", 2 pgs.

"U.S. Appl. No. 14/997,692, Non Final Office Action dated Mar. 28, 2016", 7 pgs.

"U.S. Appl. No. 14/997,692, Non Final Office Action dated Apr. 19, 2017", 10 pgs.

"U.S. Appl. No. 14/997,692, Notice of Allowance dated Jun. 10, 2016", 8 pgs.

"U.S. Appl. No. 14/997,692, Notice of Allowance dated Aug. 17, 2017", 5 pgs.

"U.S. Appl. No. 14/997,692, Notice of Allowance dated Oct. 7, 2016", 6 pgs.

"U.S. Appl. No. 14/997,692, Preliminary Amendment filed Feb. 4, 2016", 9 pgs.

"U.S. Appl. No. 14/997,692, filed Mar. 29, 2016 to Non Final Office Action dated Mar. 28, 2016", 8 pgs.

"U.S. Appl. No. 14/997,692, Response filed Jul. 19, 2017 to Non Final Office Action dated Apr. 19, 2017", 9 pgs.

"U.S. Appl. No. 15/269,591, Final Office Action dated Mar. 11, 2019", 7 pgs.

"U.S. Appl. No. 15/269,591, Non Final Office Action dated Aug. 30, 2018", 10 pgs.

"U.S. Appl. No. 15/269,591, Preliminary Amendment filed Oct. 4, 2016", 6 pgs.

"U.S. Appl. No. 15/269,591, filed Aug. 6, 2018 to Restriction Requirement dated Jun. 5, 2018", 7 pgs.

"U.S. Appl. No. 15/269,591, filed Nov. 30, 2018 to Non Final Office Action dated Aug. 30, 2018", 8 pgs.

"U.S. Appl. No. 15/269,591, Restriction Requirement dated Jun. 5, 2018", 7 pgs.

"U.S. Appl. No. 15/420,745, Advisory Action dated Mar. 9, 2018", 3 pgs.

"U.S. Appl. No. 15/420,745, Examiner Interview Summary dated Mar. 14, 2019", 3 pgs.

"U.S. Appl. No. 15/420,745, Final Office Action dated Dec. 28, 2017", 12 pgs.

"U.S. Appl. No. 15/420,745, Non Final Office Action dated Jun. 29, 2017", 14 pgs.

"U.S. Appl. No. 15/420,745, Non Final Office Action dated Nov. 8, 2018", 13 pgs.

"U.S. Appl. No. 15/420,745, Preliminary Amendment filed Feb. 14, 2017", 8 pgs.

"U.S. Appl. No. 15/420,745, filed Feb. 19, 2018 to Final Office Action dated Dec. 28, 2017", 12 pgs.

"U.S. Appl. No. 15/420,745, filed Mar. 22, 2018 to Final Office Action dated Dec. 28, 2017", 14 pgs.

"U.S. Appl. No. 15/420,745, filed Sep. 26, 2017 to Non Final Office Action dated Jun. 29, 2017", 9 pgs.

"U.S. Appl. No. 15/420,745, filed Mar. 12, 2019 to Non Final Office Action dated Nov. 8, 2018", 11 pgs.

"European Application Serial No. 08782036.1, Decision to Grant dated Jun. 6, 2013", 2 pgs.

"European Application Serial No. 08782036.1, Examination Notification Art. 94(3) dated Dec. 15, 2011", 4 pgs.

"European Application Serial No. 08782036.1, Examination Notification Art. 94(3) dated Dec. 21, 2010", 4 pgs.

"European Application Serial No. 08782036.1, Response filed Apr. 24, 2012 to Examination Notification Art. 94(3) dated Dec. 15, 2011", 9 pgs.

"European Application Serial No. 08782036.1, Response filed Apr. 28, 2011 to Examination Notification Art. 94(3) dated Dec. 21, 2010", 10 pgs.

"European Application Serial No. 08782036.1, Summons to Attend Oral Proceeding dated May 18, 2012", 5 pgs.

"European Application Serial No. 12199556.7, Examination Notification Art. 94(3) dated Feb. 11, 2014", 3 pgs.

"European Application Serial No. 12199556.7, Extended European Search Report dated Apr. 4, 2013", 5 pgs.

"European Application Serial No. 12199556.7, Office Action dated May 6, 2013", 2 pgs.

"European Application Serial No. 12199556.7, Response filed Apr. 28, 2014 to Examination Notification Art. 94(3) dated Feb. 11, 2014", 7 pgs.

"European Application Serial No. 12199556.7, Response filed Nov. 4, 2013 to Office Action dated May 6, 2013", 2 pgs.

"European Application Serial No. 12199556.7, Summons to Attend Oral Proceeding dated Jan. 21, 2015", 12 pgs.

"European Application Serial No. 12199556.7, Summons to Attend Oral Proceeding dated Feb. 4, 2015", 5 pgs.

"European Application Serial No. 12199556.7, Summons to Attend Oral Proceedings dated Mar. 30, 2015", 1 pg.

"European Application Serial No. 12199558.3, Examination Notification Art. 94(3) dated Dec. 5, 2013", 3 pgs.

"European Application Serial No. 12199558.3, Extended European Search Report dated Apr. 4, 2013", 5 pgs.

"European Application Serial No. 12199558.3, Office Action dated May 6, 2013", 2 pgs.

"European Application Serial No. 12199558.3, Response filed Apr. 4, 2014 to Examination Notification Art. 94(3) dated Dec. 5, 2013", 3 pgs.

"European Application Serial No. 12199558.3, Response filed Nov. 4, 2013 to Office Action dated May 6, 2013", 2 pgs.

"European Application Serial No. 12199558.3, Summons to Attend Oral Proceeding dated Jan. 19, 2015", 5 pgs.

(56) References Cited

OTHER PUBLICATIONS

"European Application Serial No. 12199558.3, Summons to Attend Oral Proceedings dated Mar. 30, 2015", 1 pg.
"European Application Serial No. 16156923.1, Extended European Search Report dated Sep. 29, 2016", 7 pgs.
"International Application Serial No. PCT/US2008/070429, International Preliminary Report on Patentability dated Oct. 13, 2008", 10 pgs.
"International Application Serial No. PCT/US2008/070429, International Search Report dated Oct. 29, 2008", 4 pgs.
"International Application Serial No. PCT/US2008/070429, Written Opinion dated Oct. 29, 2008", 8 pgs.
"Japanese Application Serial No. 2013-114262, Office Action dated Jan. 19, 2015", With English Translation, 5 pgs.
"Japanese Application Serial No. 2013-114262, Office Action dated Apr. 3, 2014", English Translation only, 2.
"Japanese Application Serial No. 2013-114262, Office Action dated Oct. 5, 2015", With English Translation, 7 pgs.
"Japanese Application Serial No. 2013-114262, Response filed Jul. 1, 2014 to Office Action dated Mar. 25, 2014", English Claims, 3 pgs.
"Sawtooth Wave", Wikipedia, The Free Encyclopedia, [Online] retrievded from the internet: https://en.wikipedia.org/wiki/Sawtooth_wave accessed Jun. 14, 2016, reprinted Jun. 11, 2019.
"U.S. Appl. No. 16/556,086, Preliminary Amendment filed Aug. 30, 2019", 5 pgs.
"U.S. Appl. No. 15/420,745, Corrected Notice of Allowability dated Aug. 7, 2019", 2 pgs.
"U.S. Appl. No. 15/420,745, Corrected Notice of Allowability dated Aug. 16, 2019", 3 pgs.
"U.S. Appl. No. 15/420,745, Notice of Allowance dated Jun. 13, 2019", 7 pgs.
"U.S. Appl. No. 15/420,745, Notice of Allowance dated Nov. 19, 2019", 5 pgs.
"U.S. Appl. No. 16/556,086, Non Final Office Action dated Jun. 8, 2021", 8 pgs.
"U.S. Appl. No. 16/556,086, filed Aug. 30, 2021 to Non Final Office Action dated Jun. 8, 2021", 7 pgs.
"U.S. Appl. No. 16/556,086, Non Final Office Action dated Nov. 23, 2021", 8 pgs.
"U.S. Appl. No. 16/556,086, filed Dec. 27, 2021 to Non Final Office Action dated Nov. 23, 2021", 8 pgs.

* cited by examiner

SYSTEM AND METHOD FOR SHAPED PHASED CURRENT DELIVERY

CLAIM OF PRIORITY

The present application is a continuation-in-part of U.S. application Ser. No. 15/269,591, filed Sep. 19, 2016, which is a continuation of U.S. application Ser. No. 13/893,094, filed May 13, 2013, which claims the benefit under 35 U.S.C. § 119 to U.S. Provisional Patent Application Ser. No. 61/646,773, filed May 14, 2012, and is a continuation-in-part of U.S. application Ser. No. 15/420,745, filed Jan. 31, 2017, which is a continuation of U.S. application Ser. No. 14/997,692, filed Jan. 18, 2016, now issued as U.S. Pat. No. 9,849,285, which is a continuation of U.S. patent application Ser. No. 13/231,493, filed Sep. 13, 2011, now issued as U.S. Pat. No. 9,238,138, which is a continuation of U.S. patent application Ser. No. 12/175,758, filed Jul. 18, 2008, now issued as U.S. Pat. No. 8,036,754, which claims the benefit under 35 U.S.C. § 119 to U.S. Provisional Patent Application Ser. No. 60/951,177, filed Jul. 20, 2007. The foregoing applications are hereby incorporated by reference into the present application in their entirety.

FIELD OF THE INVENTION

The present inventions relate to tissue modulation systems, and more particularly, to systems and methods for adjusting the modulation provided to tissue to optimize a therapeutic effect.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of spinal modulation has begun to expand to additional applications, such as angina pectoris and incontinence. Deep Brain Stimulation (DBS) has also been applied therapeutically for well over a decade for the treatment of refractory Parkinson's Disease, and DBS has also recently been applied in additional areas, such as essential tremor and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neuromodulation systems typically includes one or more electrode carrying modulation leads, which are implanted at the desired modulation site, and a neuromodulator device implanted remotely from the modulation site, but coupled either directly to the modulation lead(s) or indirectly to the modulation lead(s) via a lead extension. Thus, electrical pulses can be delivered from the neuromodulator device to the modulation electrode(s) to modulate or activate a volume of tissue in accordance with a set of modulation parameters and provide the desired efficacious therapy to the patient. In particular, electrical energy conveyed between at least one cathodic electrode and at least one anodic electrode creates an electrical field, which when strong enough, depolarizes (or "stimulates") the neurons beyond a threshold level, thereby inducing the firing of action potentials (APs) that propagate along the neural fibers. A typical modulation parameter set may include the electrodes that are sourcing (anodes) or returning (cathodes) the modulation current at any given time, as well as the amplitude, duration, and rate of the modulation pulses.

Electrical neuromodulation energy is typically selected to be delivered in the form of a train of electrical pulses, which are easy to generate using existing circuitry contained within the neuromodulator device. Furthermore, at a relatively low frequency, there is a one-to-one correspondence between the generation of an AP and each pulse, and therefore, the use of pulsed electrical modulation energy provides a more controlled technique for stimulating tissue.

The neuromodulation system may further comprise a handheld patient programmer to remotely instruct the neuromodulator device to generate electrical modulation pulses in accordance with selected modulation parameters. The handheld programmer in the form of a remote control (RC) may, itself, be programmed by a clinician, for example, by using a clinician's programmer (CP), which typically includes a general purpose computer, such as a laptop, with a programming software package installed thereon.

Of course, neuromodulator devices are active devices requiring energy for operation, and thus, the neuromodulation system may oftentimes includes an external charger to recharge a neuromodulator device, so that a surgical procedure to replace a power depleted neuromodulator device can be avoided. To wirelessly convey energy between the external charger and the implanted neuromodulator device, the charger typically includes an alternating current (AC) charging coil that supplies energy to a similar charging coil located in or on the neuromodulator device. The energy received by the charging coil located on the neuromodulator device can then be used to directly power the electronic componentry contained within the neuromodulator device, or can be stored in a rechargeable battery within the neuromodulator device, which can then be used to power the electronic componentry on-demand.

Typically, the therapeutic effect for any given neuromodulation application may be optimized by adjusting the modulation parameters. Often, these therapeutic effects are correlated to the diameter of the nerve fibers that innervate the volume of tissue to be modulated. For example, in SCS, activation (i.e., recruitment) of large diameter sensory fibers is believed to reduce/block transmission of smaller diameter pain fibers via interneuronal interaction in the dorsal horn of the spinal cord. Activation of large sensory fibers also typically creates a sensation known as paresthesia that can be characterized as an alternative sensation that replaces the pain signals sensed by the patient.

Although alternative or artifactual sensations are usually tolerated relative to the sensation of pain, patients sometimes report these sensations to be uncomfortable, and therefore, they can be considered an adverse side-effect to neuromodulation therapy in some cases. It has been shown that high-frequency pulsed electrical energy can be effective in providing neuromodulation therapy for chronic pain without causing paresthesia. However, the circuitry required to generate electrical pulses requires additional electrical components, e.g., switches, over other conventional circuitry. Furthermore, high-frequency pulsed electrical energy consumes an excessive amount of energy, thereby requiring the neuromodulator device to be charged more often.

There, thus, remains a need for an improved technique to treat chronic pain via neuromodulation therapy without causing uncomfortable side-effects.

SUMMARY OF THE INVENTION

In accordance with a first aspect of the present inventions, a method of treating an ailment (e.g., pain in one or both of the lower back and legs) suffered by a patient using one or more electrodes adjacent spinal column tissue of the patient is provided. The method comprises delivering electrical modulation energy from the electrode(s) to the spinal column tissue in accordance with a continuous bi-phasic waveform (e.g., one of a sinusoidal waveform, a haversine waveform, triangular waveform, a ramped waveform, and an arbitrarily-shaped continuous charge-balanced waveform), thereby modulating the spinal column tissue to treat the ailment.

The continuous bi-phasic waveform has a positive phase and a negative phase, which may be symmetrical or asymmetrical. In one method, the positive and negative phases are charge balanced. In another method, the continuous bi-phasic waveform may be amplitude-modulated. In still another method, the continuous bi-phasic waveform is discretized. The continuous bi-phasic waveform may have a frequency in the range of 2 Hz-100 KHz, preferably in the range of 1 KHz-50 KHz, and more preferably in the range of 3 KHz-15 KHz. Preferably, the electrical modulation energy is delivered from the electrode(s) to the spinal column tissue in accordance with the continuous bi-phasic waveform without causing an uncomfortable side-effect in the patient.

In accordance with a second aspect of the present inventions, an implantable electrical modulation system is provided. The electrical modulation system comprises one or more electrical terminals configured for being coupled to one or more modulation leads, and output modulation circuitry capable of outputting electrical modulation energy to the one or more electrical terminals in accordance with a continuous bi-phasic waveform. The control circuitry configured for modifying a shape of the continuous bi-phasic waveform, thereby changing the characteristics of the electrical modulation energy outputted to the electrode(s). In one embodiment, the control circuitry is configured for modifying the shape of the continuous bi-phasic waveform by selecting one of a plurality of different waveform shape types comprising at least two of a sinusoidal waveform, a haversine waveform, triangular waveform, and a ramped waveform.

The continuous bi-phasic waveform has a positive phase and a negative phase, which may be symmetrical or asymmetrical. In one embodiment, the positive and negative phases are charge balanced. In another embodiment, the continuous bi-phasic waveform may be amplitude-modulated. In still another embodiment, the continuous bi-phasic waveform is discretized. The continuous bi-phasic waveform may have a frequency in the range of 2 Hz-100 KHz, preferably in the range of 1 KHz-50 KHz, and more preferably in the range of 3 KHz-15 KHz. In an optional embodiment, the control circuitry is configured for selecting between the continuous bi-phasic waveform and a pulsed waveform in response to a user input.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal column modulation (SCM) system. However, it is to be understood that the while the invention lends itself well to applications in SCM, the invention, in its broadest aspects, may not be so limited. Rather, the invention may be used with any type of implantable electrical circuitry used to modulate tissue. For example, the present invention may be used as part of a pacemaker, a defibrillator, a cochlear modulator device, a retinal modulator device, a modulator device configured to produce coordinated limb movement, a cortical modulator device, a deep brain modulator device, peripheral nerve modulator device, micromodulator device, or in any other tissue modulator device configured to treat urinary incontinence, sleep apnea, shoulder sublaxation, headache, etc.

Figure 1:
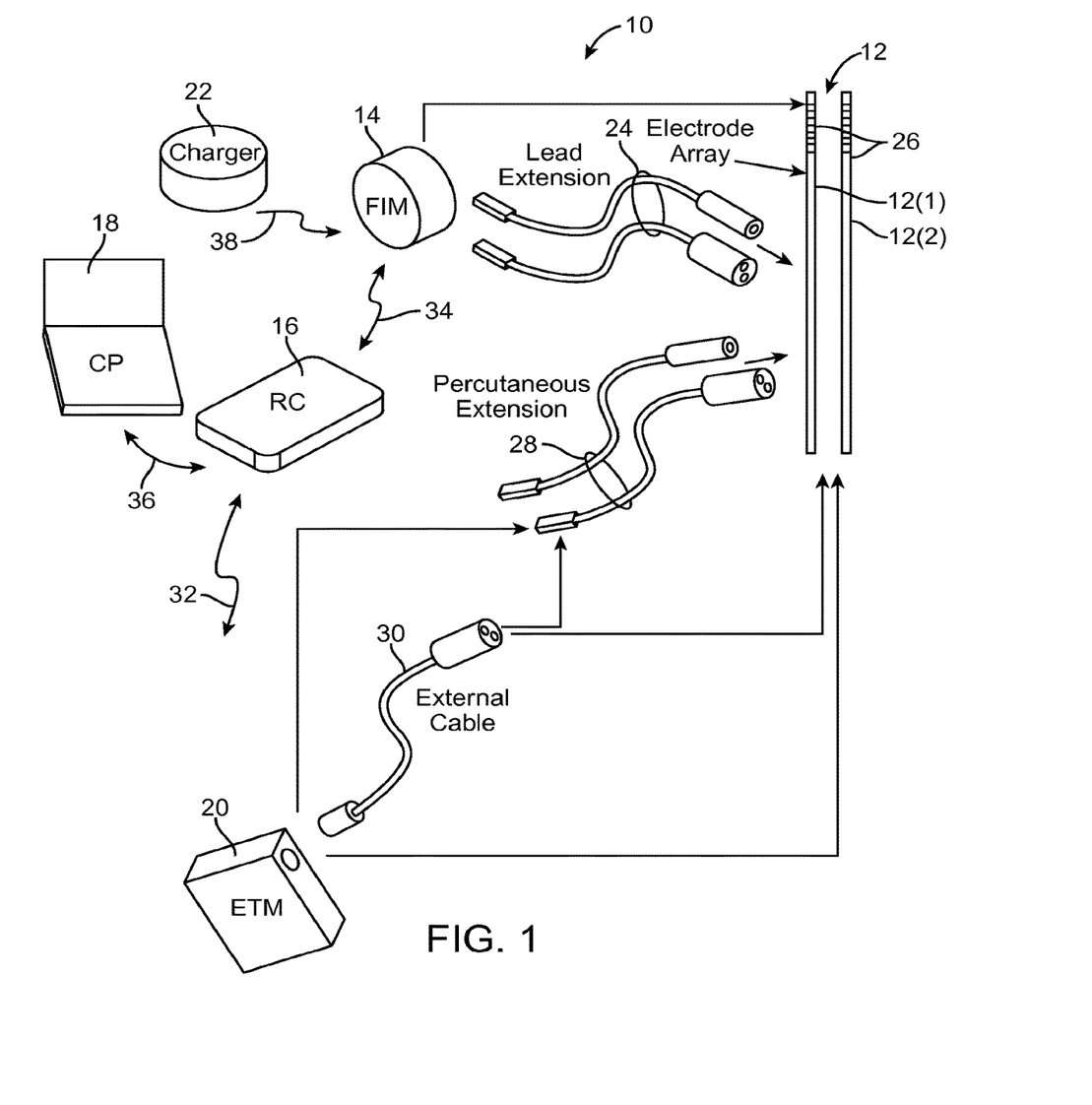
FIG. 1 is plan view of one embodiment of a spinal column modulation (SCM) system arranged in accordance with the present inventions.

Turning first to FIG. 1, an exemplary SCM system 10 generally includes one or more (in this case, two) implantable modulation leads 12(1) and 12(2), a fully implantable modulator (FIM) 14, an external remote controller RC 16, a clinician's programmer (CP) 18, an External Trial Modulator (ETM) 20, and an external charger 22.

The FIM 14 is physically connected via one or more percutaneous lead extensions 24 to the modulation leads 12, which carry a plurality of electrodes 26 arranged in an array.

In the illustrated embodiment, the modulation leads 12 are percutaneous leads, and to this end, the electrodes 26 are arranged in-line along the modulation leads 12. In alternative embodiments, the electrodes 26 may be arranged in a two-dimensional pattern on a single paddle lead. As will be described in further detail below, the FIM 14 includes waveform generation circuitry that delivers the electrical modulation energy in the form of a continuous electrical waveform to the electrode array 26 in accordance with a set of modulation parameters.

The ETM 20 may also be physically connected via the percutaneous lead extensions 28 and external cable 30 to the modulation leads 12. The ETM 20, which has similar waveform generation circuitry as the FIM 14, also delivers electrical modulation energy in the form of an electrical waveform to the electrode array 26 accordance with a set of modulation parameters. The major difference between the ETM 20 and the FIM 14 is that the ETM 20 is a non-implantable device that is used on a trial basis after the modulation leads 12 have been implanted and prior to implantation of the FIM 14, to test the responsiveness of the modulation that is to be provided. Thus, any functions described herein with respect to the FIM 14 can likewise be performed with respect to the ETM 20. Further details of an exemplary ETM are described in U.S. Pat. No. 6,895,280, which is expressly incorporated herein by reference.

The RC 16 may be used to telemetrically control the ETM 20 via a bi-directional RF communications link 32. Once the FIM 14 and modulation leads 12 are implanted, the RC 16 may be used to telemetrically control the FIM 14 via a bi-directional RF communications link 34. Such control allows the FIM 14 to be turned on or off and to be programmed with different modulation parameter sets. The FIM 14 may also be operated to modify the programmed modulation parameters to actively control the characteristics of the electrical modulation energy output by the FIM 14. The CP 18 provides clinician detailed modulation parameters for programming the FIM 14 and ETM 20 in the operating room and in follow-up sessions. The CP 18 may perform this function by indirectly communicating with the FIM 14 or ETM 20, through the RC 16, via an IR communications link 36. Alternatively, the CP 18 may directly communicate with the FIM 14 or ETM 20 via an RF communications link (not shown).

The external charger 22 is a portable device used to transcutaneously charge the FIM 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the FIM 14 has been programmed, and its power source has been charged by the external charger 22 or otherwise replenished, the FIM 14 may function as programmed without the RC 16 or CP 18 being present.

Figure 2:
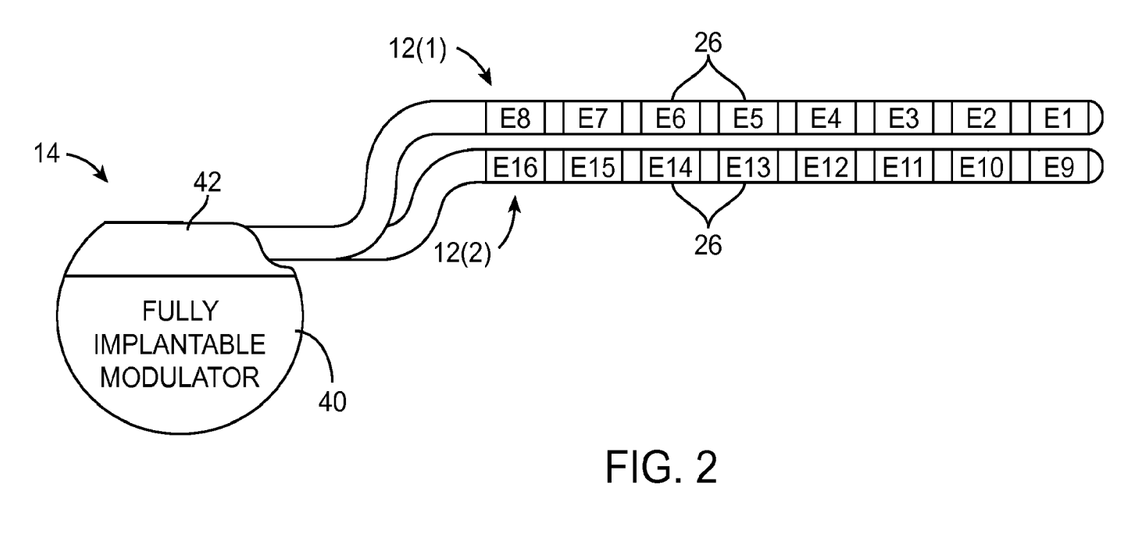
FIG. 2 is a profile view of a fully implantable modulator (FIM) used in the SCM system of FIG. 1.

Referring now to FIG. 2, the external features of the modulation leads 12 and the FIM 14 will be briefly described. One of the modulation leads 12(1) has eight electrodes 26 (labeled E1-E8), and the other modulation lead 12(2) has eight electrodes 26 (labeled E9-E16). The actual number and shape of leads and electrodes will, of course, vary according to the intended application. The FIM 14 comprises an outer case 40 for housing the electronic and other components (described in further detail below), and a connector 42 to which the proximal ends of the modulation leads 12 mates in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

As will be described in further detail below, the FIM 14 includes circuitry that delivers the electrical modulation energy in the form of a continuous bi-phasic waveform to the electrode array 26 in accordance with a set of modulation parameters. Such modulation parameters may comprise electrode combinations, which define the electrodes that are activated as anodes (positive), cathodes (negative), and turned off (zero), and electrical parameters, which define the amplitude (measured in milliamps or volts depending on whether the FIM 14 supplies constant current or constant voltage to the electrode array 26), cycle duration (measured in microseconds), and frequency (measured in cycles per second), and as will be described in further detail below, a waveform shape. If the continuous bi-phasic waveform is symmetrical, the frequency will correspond to the phase duration; however, as will be discussed in further detail below, if the continuous bi-phasic waveform is asymmetrical, the duration of the waveform phases will be different from each other. In an optional embodiment, the circuitry may also deliver electrical stimulation energy in the form of a conventional pulsed waveform to the electrode array 26 in accordance with a set of stimulation parameters, which in addition to an electrode combination, may include pulse amplitude, pulse duration, and pulse rate.

Electrical modulation will occur between two (or more) active electrodes, one of which may be the FIM case. Modulation energy may be transmitted to the tissue in a monopolar or multipolar (e.g., bipolar, tripolar, etc.) fashion. Monopolar modulation occurs when a selected one of the lead electrodes 26 is activated along with the case of the FIM 14, so that modulation energy is transmitted between the selected electrode 26 and case. Bipolar modulation occurs when two of the lead electrodes 26 are activated as anode and cathode, so that modulation energy is transmitted between the selected electrodes 26. For example, electrode E3 on the first lead 12 may be activated as an anode at the same time that electrode E11 on the second lead 12 is activated as a cathode. Tripolar modulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

Figure 3A:
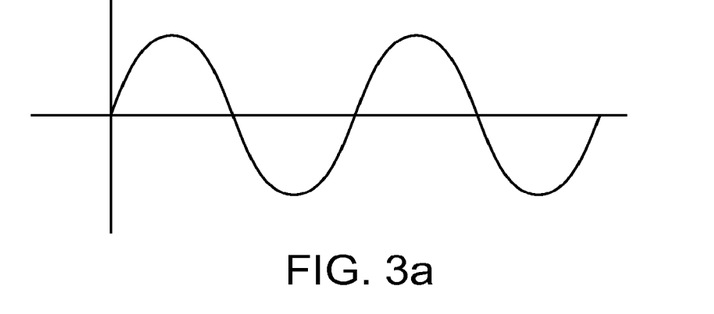
FIGS. 3a-3f are diagrams of various continuous bi-phasic waveforms that can be generated by the system of FIG. 1.
Figure 3B:
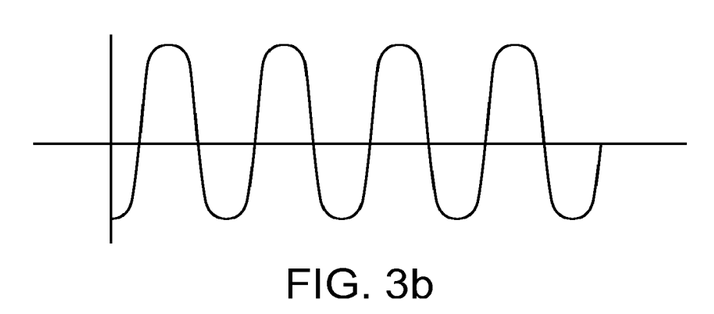
Figure 3C:
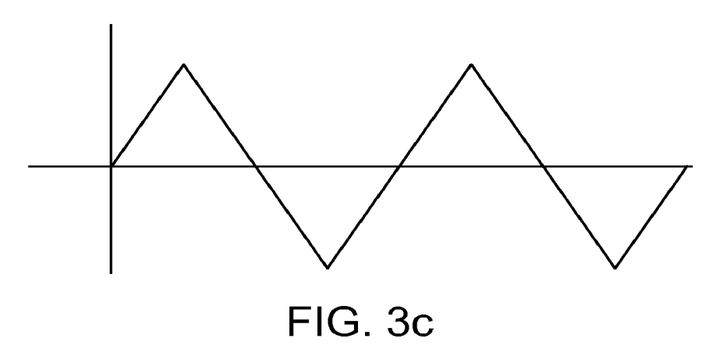
Figure 3D:
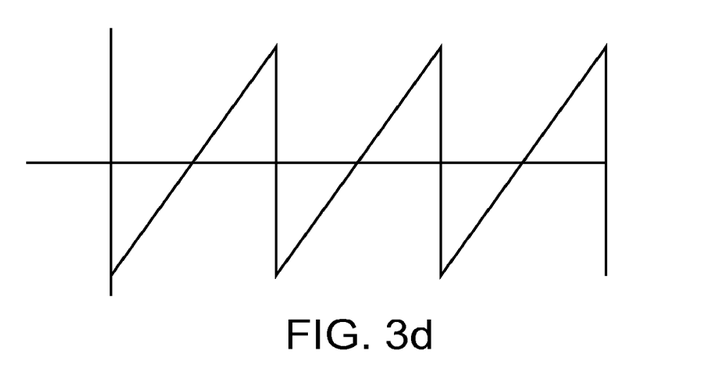
Figure 3E:
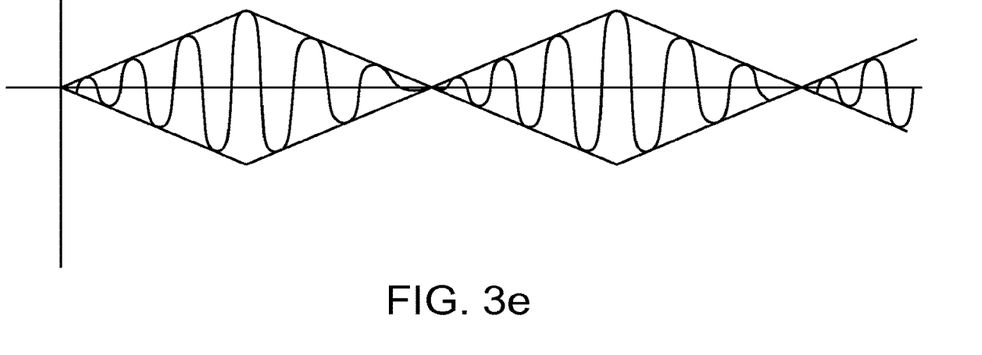

Referring to FIGS. 3a-3d, the continuous bi-phasic waveform may include any one of a plurality of different types of waveforms including, e.g., a sinusoidal waveform (FIG. 3a), a haversine waveform (FIG. 3b), a triangular waveform (FIG. 3c), or a ramped waveform (FIG. 3d). In one embodiment, the FIM 14 is capable of outputting only one type of continuous bi-phasic waveform. In an optional embodiment, the FIM 14 is capable of selectively outputting any of the continuous bi-phasic waveforms. The continuous bi-phasic waveform is alternating and has a positive phase (i.e., the portion of the waveform that has a positive polarity) and a negative phase (i.e., the portion of the waveform that has a negative polarity). In an optional embodiment, the continuous bi-phasic waveform may be amplitude modulated. For example, as shown in FIG. 3e, the peak amplitudes of the positive and negative phases of a sinusoidal waveform are modulated in accordance with an amplitude modulating triangular waveform.

Figure 3F:
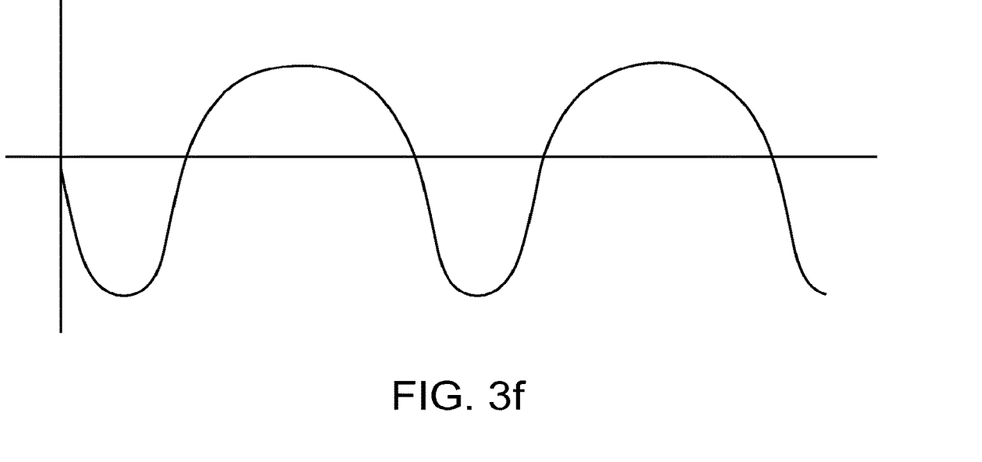

In one embodiment, the positive and negative phases of the waveform may be symmetrical (i.e., the positive and negative phases have the same amplitude, duration, and shape, but inverted relative to each other, as shown in FIGS. 3a-3e. In another embodiment, the positive and negative phases of the waveform may be asymmetrical. For example, as shown in FIG. 3f, each negative phase cycle of the sinusoidal waveform has a larger peak amplitude, but shorter duration, relative to each positive phase cycle of the sinusoidal waveform. This may be useful, e.g., if one of the phases has a greater effect on modulating spinal column tissue than the other phase. Preferably, the positive and negative phases are charge balanced in order to prevent build up of tissue charge and damage to the electrodes 26. For example, as shown in FIG. 3f, each positive phase cycle of the sinusoidal waveform has a longer duration than each negative phase cycle of the sinusoidal waveform to compensate for the smaller amplitude, thereby charge balancing the positive and negative phases. The parameters of the continuous waveform may be individually programmable (e.g., the amplitude, duration, and frequency may be modified), and if the positive and negative phases of the continuous waveform are asymmetric, the parameters of these phases (e.g., the amplitude and duration) may be independently changed relative to each other.

The continuous bi-phasic waveform may have a frequency in the range of 2 Hz-100 KHz; however, so that the continuous bi-phasic waveform is high frequency in nature, it preferably has a frequency in the range of 1 KHz-50 KHz, and more preferably in the range of 3 KHz-15 KHz. It can be appreciated that, because high frequency modulation modulates neural axons to provide a therapeutic effect in a manner that does not necessarily evoke action potentials, the high frequency modulation energy need not be pulsed. That is, whereas low frequency modulation provides therapy by creating a one-to-one correspondence between pulses and the generation of action potentials, high frequency modulation does not necessarily operate on this principle, and therefore, pulses are not required. It is believed that high frequency continuous waveforms can be more energy efficient than high frequency pulsed waveforms, because they may require less complicated circuitry than that required by high frequency pulsed waveforms.

Figure 4:
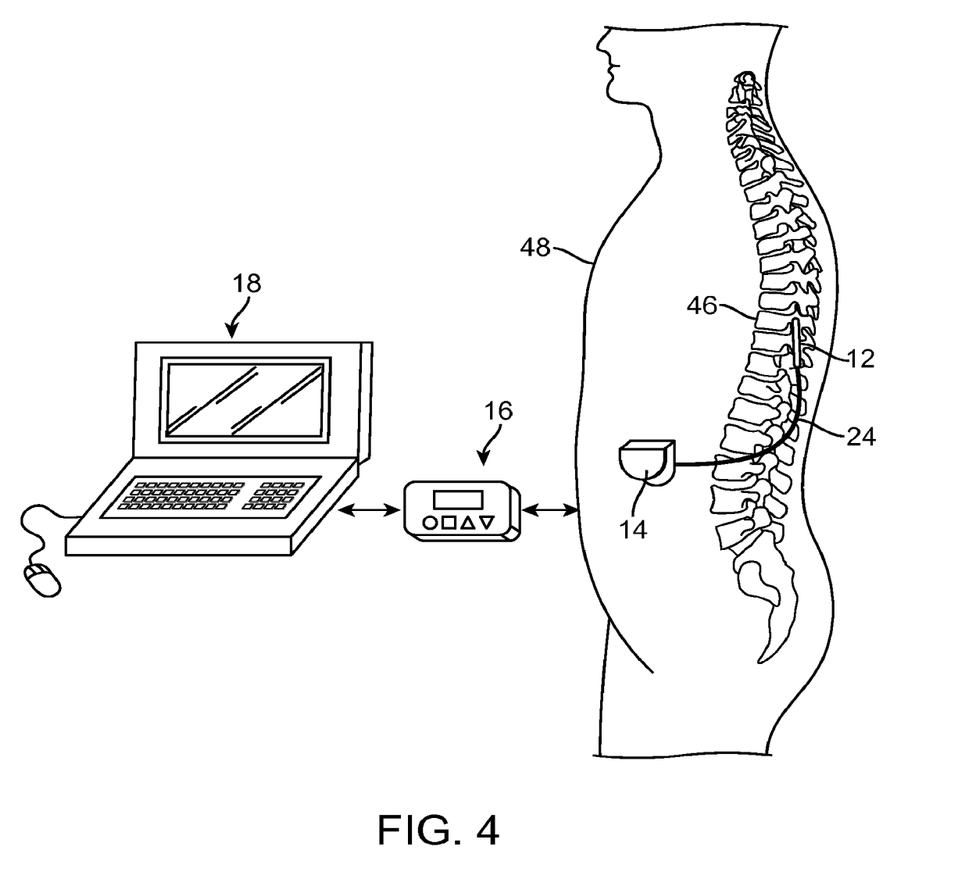
FIG. 4 is a plan view of the SCM system of FIG. 1 in use with a patient.

As shown in FIG. 4, the modulation leads 12 are implanted within the spinal column 46 of a patient 48. The preferred placement of the modulation leads 12 is adjacent, i.e., resting near, the spinal column area to be modulated. The modulation leads 12 will be located in a vertebral position that depends upon the location and distribution of the chronic pain. For example, if the chronic pain is in the lower back or legs, the modulation leads 12 may be located in the mid- to low-thoracic region (e.g., at the T9-12 vertebral levels). Due to the lack of space near the location where the electrode leads 12 exit the spinal column 46, the FIM 14 is generally implanted in a surgically-made pocket either in the abdomen or above the buttocks. The FIM 14 may, of course, also be implanted in other locations of the patient's body. The lead extensions 24 facilitate locating the FIM 14 away from the exit point of the electrode leads 12. As there shown, the CP 18 communicates with the FIM 14 via the RC 16.

Figure 5:
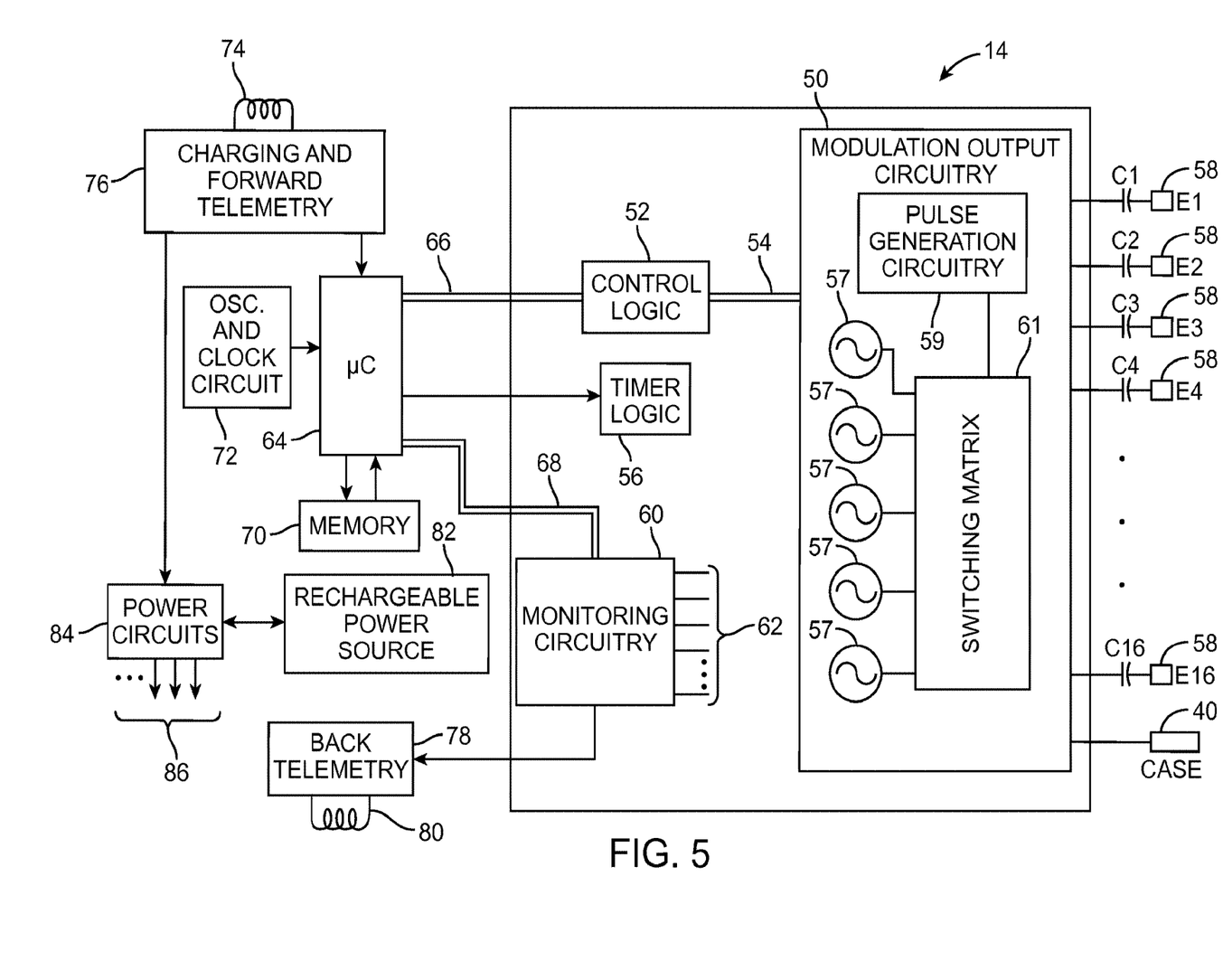
FIG. 5 is a block diagram of the internal components of the FIM of FIG. 2.

Turning next to FIG. 5, one exemplary embodiment of the FIM 14 will now be described. The FIM 14 includes modulation output circuitry 50 configured for generating electrical modulation energy in accordance with a continuous bi-phasic waveform (e.g., any one of the waveforms illustrated in FIGS. 3a-3e) having a specified amplitude, frequency, phase duration, and shape under control of control logic 52 over data bus 54. Control of the frequency and phase duration of the waveform is facilitated by analog circuitry, or digital timer logic circuitry 56 controlling the analog circuitry, and which may have a suitable resolution, e.g., 10p. The modulation energy generated by the modulation output circuitry 50 is output via capacitors C1-C16 to electrical terminals 58 corresponding to electrodes E1-E16.

In the illustrated embodiment, the modulation output circuitry 50 comprises a plurality of oscillators 57 capable of respectively supplying modulation energy to the electrical terminals 58. These oscillators 57 may be current-controlled and/or voltage controlled. In an alternative embodiment, the number of oscillators 57 is less than the number of electrical terminals 58 (e.g., only one oscillator may be provided), in which case, the oscillator(s) 57 may be coupled to the electrical terminals 58 via the capacitors C1-C16 through a low impedance switching matrix 61 that can be operated to selectively coupled the oscillator(s) 57 to the desired electrical terminals 58. In another embodiment, the oscillators 57 may respectively output different continuous bi-phasic waveform shapes. In this case, any one of the different continuous bi-phasic waveform shapes can be selectively output to the electrical terminals 58 via operation of the switching matrix 61.

In an optional embodiment, the modulation output circuitry 50 comprises conventional electrical pulse generation circuitry 59 that can be operated in conjunction with the oscillators 57 to provide a means for selectively outputting a continuous bi-phasic waveform or a pulsed waveform to selected electrical terminals 58 (and thus electrodes 26). In one embodiment, the current through each electrical terminal 58 can be individually set from 0 to ±10 mA in steps of 100 μA, within the output voltage/current requirements of the FIM 14. Additionally, in one embodiment, the total current output by a group of electrical terminals 58 can be up to ±20 mA (distributed among the electrodes included in the group). Moreover, it is seen that each of the electrical terminals 58 can operate in a multipolar mode, e.g., where two or more electrical terminals are grouped to generate the continuous waveform. Alternatively, each of the electrical terminals 58 can operate in a monopolar mode where, e.g., one or more electrical terminals 58 are grouped with the case of the FIM 14.

It can be appreciated that an electrical terminal 58 may be assigned an amplitude and included with any of up to k possible groups, where k is an integer corresponding to the number of channels, and in one embodiment, is equal to 4, and with each channel k having a defined amplitude, frequency, phase duration, and waveform shape. Other channels may be realized in a similar manner. Thus, each channel identifies which electrical terminals 58 (and thus electrodes) are selected to synchronously generate a continuous bi-phasic waveform defined in accordance with an amplitude, frequency, phase duration, and waveform shape.

Figure 6:
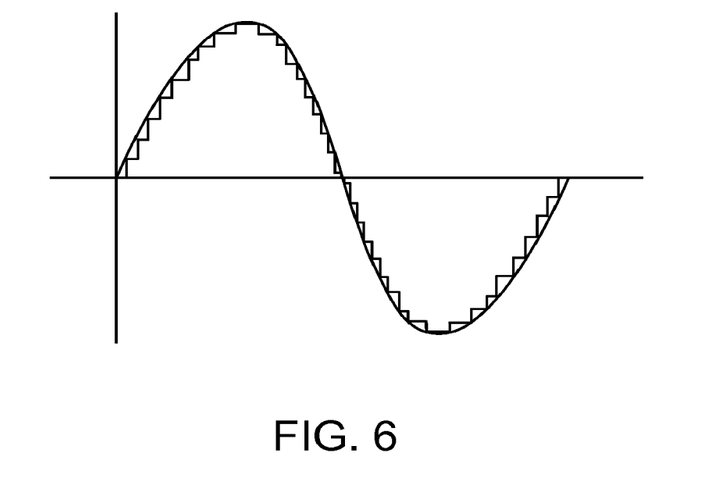
FIG. 6 is a diagram of a discretized approximation of a continuous bi-phasic waveform that can be generated by the FIM of FIG. 2.

In an alternative embodiment, rather than using oscillators, the pulse generation circuitry 59 can be used to generate a discretized waveform that approximates the continuous bi-phasic waveform. That is, the continuous bi-phasic waveform can be formed of a stepwise function of amplitude levels. For example, as shown in FIG. 6, the positively sloping portion of the continuous sinusoidal waveform can be formed by a series of gradually increasing amplitude levels, while the negatively sloping portion of the continuous sinusoidal waveform can be formed by a series of gradually decreasing amplitude levels. As such, a good approximation of any continuous waveform can be made by the pulse generation circuitry 59. Individual channels k may be time multiplexed to construct the discrete approximations of the continuous bi-phasic waveforms.

The FIM 14 also comprises monitoring circuitry 60 for monitoring the status of various nodes or other points 62 throughout the FIM 14, e.g., power supply voltages, temperature, battery voltage, and the like. The FIM 14 further comprises processing circuitry in the form of a microcontroller (μC) 64 that controls the control logic 52 over data bus 66, and obtains status data from the monitoring circuitry 60 via data bus 68. The FIM 14 additionally controls the timer logic 56. The FIM 14 further comprises memory 70 and oscillator and clock circuit 72 coupled to the microcontroller 64. The microcontroller 64, in combination with the memory 70 and oscillator and clock circuit 72, thus comprise a microprocessor system that carries out a program function in accordance with a suitable program stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the FIM 14 in accordance with a selected operating program and modulation parameters. In controlling the operation of the FIM 14, the microcontroller 64 is able to individually generate the electrical waveforms at the electrodes 26 using the modulation output circuitry 50, in combination with the control logic 52 and timer logic 56, thereby allowing each electrode 26 to be paired or grouped with other electrodes 26, including the monopolar case electrode, to control the polarity, amplitude, rate, waveform width and channel through which the electrical waveforms are provided.

The FIM 14 further comprises an alternating current (AC) receiving coil 74 for receiving programming data (e.g., the operating program and/or modulation parameters) from the RC 16 and/or CP 18 in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the FIM 14.

The FIM 14 further comprises back telemetry circuitry 78 and an alternating current (AC) transmission coil 80 for sending informational data sensed through the monitoring circuitry 60 to the RC 16 and/or CP 18. The back telemetry features of the FIM 14 also allow its status to be checked. For example, when the RC 16 and/or CP 18 initiates a programming session with the FIM 14, the capacity of the battery is telemetered, so that the RC 16 and/or CP 18 can calculate the estimated time to recharge. Any changes made to the current stimulus parameters are confirmed through back telemetry, thereby assuring that such changes have been correctly received and implemented within the implant system. Moreover, upon interrogation by the RC 16 and/or CP 18, all programmable settings stored within the FIM 14 may be uploaded to the RC 16 and/or CP 18.

The FIM 14 further comprises a rechargeable power source 82 and power circuits 84 for providing the operating power to the FIM 14. The rechargeable power source 82 may, e.g., comprise a lithium-ion or lithium-ion polymer battery. The rechargeable battery 82 provides an unregulated voltage to the power circuits 84. The power circuits 84, in turn, generate the various voltages 86, some of which are regulated and some of which are not, as needed by the various circuits located within the FIM 14. The rechargeable power source 82 is recharged using rectified AC power (or DC power converted from AC power through other means, e.g., efficient AC-to-DC converter circuits, also known as "inverter circuits") received by the AC receiving coil 74. To recharge the power source 82, an external charger (not shown), which generates the AC magnetic field, is placed against, or otherwise adjacent, to the patient's skin over the implanted FIM 14. The AC magnetic field emitted by the external charger induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications (e.g., programming and control data) and charging energy from the external device, it should be appreciated that the AC receiving coil 74 can be arranged as a dedicated charging coil, while another coil, such as coil 80, can be used for bi-directional telemetry.

Additional details concerning the above-described and other FIMs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an FIM, the SCM system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the modulation in accordance with the control signals.

Figure 7:
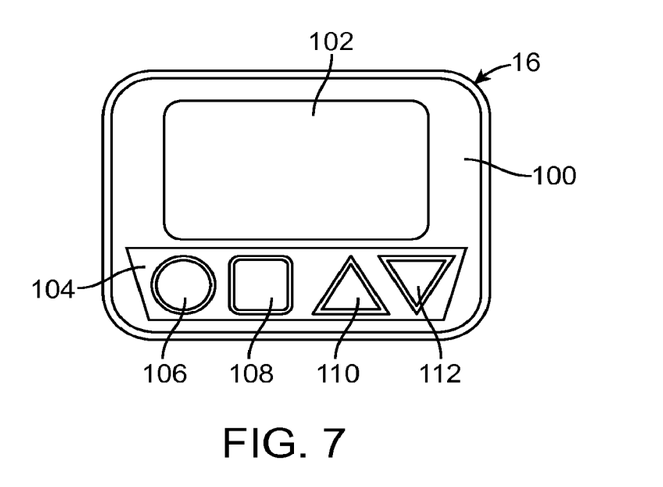
FIG. 7 is a plan view of a hand-held remote control (RC) that can be used in the SCM system of FIG. 1.

Referring now to FIG. 7, one exemplary embodiment of an RC 16 will now be described. As previously discussed, the RC 16 is capable of communicating with the FIM 14, CP 18, or ETM 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the FIM 14 to be turned ON and OFF, provide for the adjustment or setting of modulation parameters within the FIM 14, and provide for selection between screens.

In the illustrated embodiment, the button 106 serves as an ON/OFF button that can be actuated to turn the IPG 14 ON and OFF. The button 108 serves as a select button that allows the RC 16 to switch between screen displays and/or parameters. The buttons 110 and 112 serve as up/down buttons that can actuated to increment or decrement any of modulation parameters of the waveform generated by the FIM 14, including waveform amplitude, waveform width, waveform rate, and waveform shape. For example, the selection button 108 can be actuated to place the RC 16 in an "Amplitude Adjustment Mode," during which the amplitude of the waveform can be adjusted via the up/down buttons 110, 112, a "Frequency Adjustment Mode," during which the frequency of the waveform can be adjusted via the up/down buttons 110, 112, and a "Shape Adjustment Mode," during which the shape of the waveform can be adjusted via the up/down buttons 110, 112. The selection button 108 can also be actuated to place the RC 16 in an "Asymmetry Mode," during which the amplitudes and duration of the positive and negative phases can be individually adjusted via the up/down buttons 110, 112. Alternatively, dedicated up/down buttons can be provided for each modulation parameter. Rather than using up/down buttons, any other type of actuator, such as a dial, slider bar, or keypad, can be used to increment or decrement the modulation parameters.

Figure 8:
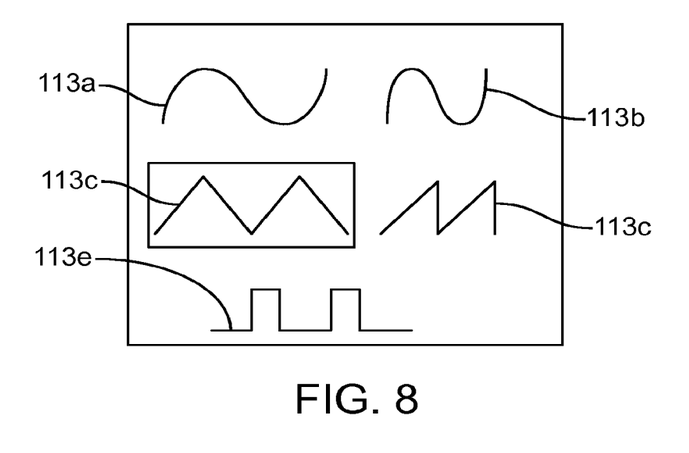
FIG. 8 is a plan view of a display screen generated by the RC of FIG. 7 to provide a means for the user to select a waveform shape type.

Significant to the present inventions, placement of the RC 16 in the Shape Adjustment Mode allows the user to select the type of continuous waveform. For example, FIG. 8 illustrates an exemplary display screen having identifiers in the form of icons, although text can be alternatively or optionally used. In particular, the display screen includes a sinusoidal waveform icon 113a, a haversine waveform icon 113b, a triangular waveform icon 113c, or a ramped waveform icon 113d that a user may scroll through and highlight (triangular waveform icon 113c shown identified) by actuating the up/down buttons 110, 112. The button 108 can be actuated to then select the highlighted waveform shape type. Alternatively, rather than highlighting a waveform icon 113 by scrolling up/down using the up/down buttons 110, 112, a check box (not shown) associated with each waveform shape type can be checked by, e.g., touching it with a stylet or finger in the case where the display screen 102 has touchscreen capabilities. Alternatively, a single-button toggle may be used to switch between the different waveform shape types. In an optional embodiment, the display screen includes a pulsed waveform icon 113e that a user may scroll through and highlight by actuating the up/down buttons 110, 112, and selected by actuating the button 108.

Figure 9:
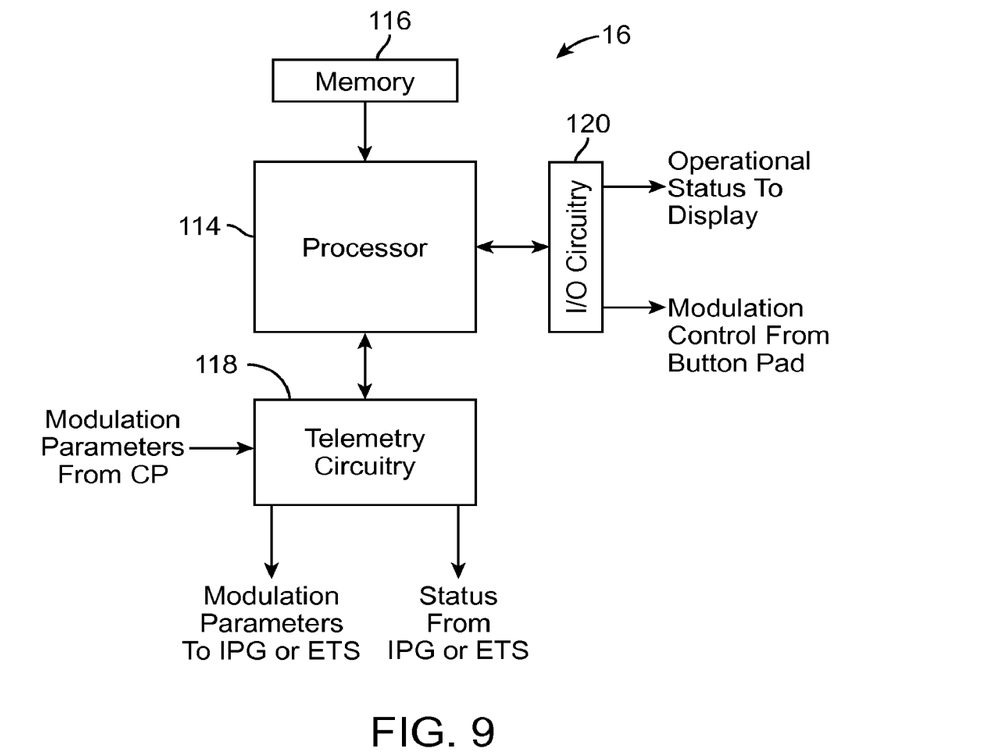
FIG. 9 is a block diagram of the internal components of the RC of FIG. 7.

Referring to FIG. 9, the internal components of an exemplary RC 16 will now be described. The RC 16 generally includes a processor 114 (e.g., a microcontroller), memory 116 that stores an operating program for execution by the processor 114, as well as modulation parameters, input/output circuitry, and in particular, telemetry circuitry 118 for outputting modulation parameters to the FIM 14 and receiving status information from the FIM 14, and input/output circuitry 120 for receiving modulation control signals from the button pad 104 and transmitting status information to the display screen 102 (shown in FIG. 7). As well as controlling other functions of the RC 16, which will not be described herein for purposes of brevity, the processor 114 generates a plurality of modulation parameter sets that define the amplitude, phase duration, frequency, and waveform shape in response to the user operation of the button pad 104. These new modulation parameter sets would then be transmitted to the FIM 14 via the telemetry circuitry 118, thereby adjusting the modulation parameters stored in the FIM 14 and/or programming the FIM 14. The telemetry circuitry 118 can also be used to receive modulation parameters from the CP 18. Further details of the functionality and internal componentry of the RC 16 are disclosed in U.S. Pat. No. 6,895,280, which has previously been incorporated herein by reference.

As described above with respect to the FIM 14, the waveform shape and the other waveform parameters are modified independent from each other. In this case, the processor 114 is configured for defining the waveform shape and the other waveform parameters in each modulation parameter set independent of each other. However, if the waveform shape and the other waveform parameters are advantageously modified dependent upon each other, the processor 114 may be configured for defining the waveform shape and the other waveform parameters in each modulation parameter set dependent upon each other; for example, by defining the other waveform parameters in response to the definition of a waveform shape to maintain the electrical charge between the modulation parameter sets uniform.

Although the foregoing programming functions have been described as being at least partially implemented in the RC 16, it should be noted that these techniques may be at least, in part, be alternatively or additionally implemented in the CP 18. Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method implemented using one or more electrodes adjacent spinal column tissue, an implantable device, and an external device, the method comprising:
   treating an ailment suffered by a patient, including:
   using the external device to receive a first user input to select a waveform shape type from a group of predefined waveform shape types that are available for selection and presented on a display of the external device;
   using the external device to receive a second user input and respond to the received user input to provide a user-adjusted waveform based on the selected waveform shape type; and
   using the implantable device to deliver electrical modulation energy from the one or more electrodes to the spinal column tissue in accordance with the user-adjusted waveform.

2. The method of claim 1, wherein:
   the waveform shape type has a first phase and a second phase; and
   the using the external device to receive the second user input and respond to the received user input by independently adjusting one of the first phase or the second phase of the user-selected waveform shape type without adjusting the other of the first phase or the second phase.

3. The method of claim 2 further comprising using the external device to receive an asymmetry mode selection user input and respond to the received asymmetry mode selection user input by entering an asymmetry mode during which the external device may be used to receive the second user input.

4. The method of claim 2 wherein the user-selected waveform shape type includes a biphasic waveform, the first phase includes a positive phase, and the second phase includes a negative phase.

5. The method of claim 4 wherein the biphasic waveform includes a continuous waveform.

6. The method of claim 2, wherein the at least one parameter of the first phase includes at least one of an amplitude or a duration and the at least one parameter of the second phase includes at least one of an amplitude or a duration.

7. The method of claim 6, further comprising adjusting an amplitude of the second phase to be larger than an amplitude of the first phase and adjusting a duration of the second phase to be smaller than a duration of the first phase.

8. The method of claim 4, wherein the positive phase and the negative phase of the biphasic waveform are charge balanced.

9. The method of claim 4, the at least one biphasic waveform includes at least one continuous biphasic waveform or discretized continuous biphasic waveform with a frequency in the range of 2 Hz-100 KHz.

10. The method of claim 4, wherein the bi-phasic waveform includes at least one continuous biphasic waveform or discretized continuous biphasic waveform with a frequency in the range of 3 KHz-15 KHz.

11. A system for treating an ailment suffered by a patient using one or more electrodes adjacent spinal column tissue, the system comprising:
   one or more electrical terminals configured for being coupled to the one or more electrodes adjacent to the spinal column tissue via one or more modulation leads;
   a user interface configured to receive a first user input to receive a user selection of a waveform shape type from a group of predefined waveform shape types that are available for selection and presented on a display of the external device, and to receive a second user input to adjust the waveform;
   control circuitry configured to receive the first and second user input from the user interface and to respond to the received second user input to provide a user-adjusted waveform based on the selected waveform shape type; and
   output modulation circuitry configured to deliver electrical modulation energy from the one or more electrodes to the spinal column tissue in accordance with the user-adjusted waveform.

12. The system of claim 11, wherein:
   the waveform shape type has a first phase and a second phase; and
   the control circuitry is configured to respond to the received second user input by independently adjusting one of the first phase or the second phase of the user-selected waveform shape type without adjusting the other of the first phase or the second phase.

13. The system of claim 12 wherein the user interface is further configured to receive an asymmetry mode selection user input and respond to the received asymmetry mode selection user input by entering an asymmetry mode during which the user interface may be used to receive the second user input.

14. The system of claim 12 wherein the user-selected waveform shape type includes a biphasic waveform, the first phase includes a positive phase, and the second phase includes a negative phase.

15. The system of claim 14 wherein the biphasic waveform includes a continuous waveform.

16. The system of claim 12, wherein the at least one parameter of the first phase includes an amplitude and a duration and the at least one parameter of the second phase includes an amplitude and a duration.

17. The system of claim 16, wherein the control circuitry is further configured to adjust an amplitude of the second phase to be larger than an amplitude of the first phase and adjust a duration of the second phase to be smaller than a duration of the first phase.

18. The system of claim 14, wherein the one or more electrical terminals and the output modulation circuitry are part of an implantable pulse generator and the user interface and control circuitry are part of a clinician's programmer.

19. The system of claim 14, wherein the biphasic waveform includes at least one continuous biphasic waveform or discretized continuous biphasic waveform with a frequency in the range of 1 KHz-50 KHz.

20. The system of claim 14, wherein the bi-phasic waveform includes at least one continuous biphasic waveform or discretized continuous biphasic waveform with a frequency in the range of 3 KHz-15 KHz.

* * * * *